US00PP21097P2

(12) United States Plant Patent
Perkins

(10) Patent No.: US PP21,097 P2
(45) Date of Patent: Jun. 22, 2010

(54) ***SALVIA* PLANT NAMED 'MES AZUR'**

(50) Latin Name: ***Salvia*×hybrid**
Varietal Denomination: Mes Azur

(75) Inventor: Ralph T. Perkins, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 56 days.

(21) Appl. No.: 12/313,156

(22) Filed: Nov. 18, 2008

(51) Int. Cl.
*A01H 5/00* (2006.01)

(52) U.S. Cl. ..... Plt./475

(58) Field of Classification Search ..... Plt./475
See application file for complete search history.

(56) References Cited

U.S. PATENT DOCUMENTS

PP19,788 P2 * 3/2009 Danziger ..... Plt./475

OTHER PUBLICATIONS

UPOV ROM GTITM Computer Database, GTI Jouve Retrieval Software 2009/04 Citation for 'Mesazur'.*

* cited by examiner

*Primary Examiner*—Wendy C. Haas
(74) *Attorney, Agent, or Firm*—S. Matthew Edwards

(57) ABSTRACT

A new *Salvia* plant named 'Mes Azur,' particularly distinguished by medium violet flower color, upright, well branched, dense and bushy habit, medium green foliage and large sized flowers that are early flowering.

1 Drawing Sheet

Latin name of the genus and species of the plant claimed: *Salvia*×hybrid.

Varietal denomination: 'Mes Azur'.

BACKGROUND OF THE NEW PLANT

The present invention comprises a new *Salvia*, botanically known as *Salvia*×hybrid, and hereinafter referred to by the variety name 'Mes Azur'.

'Mes Azur' is a product of a planned breeding program. The new cultivar 'Mes Azur' has medium violet flower color, upright, well branched, dense and bushy habit, medium green foliage and large sized flowers that are early flowering.

'Mes Azur' originated from an hybridization in a controlled breeding program in Gilroy, Calif. USA. The female parent was an unpatented, proprietary hybrid seedling (*Salvia greggii*×*S. microphylla*) identified as 'F15-1' with lavender-rose color. 'F15-1' has a more open habit and smaller foliage than 'Mes Azur'.

The male parent of 'Mes Azur' was an unpatented, proprietary hybrid seeding (*Salvia greggii*×*Salvia hybrida*) identified as '47-1' with rose color. '47-1' has a much taller and leggy plant habit and smaller foliage than 'Mes Azur'.

'Mes Azur' was selected as one flowering plant within the progeny of the stated cross in September 2004 in a controlled environment in Gilroy, Calif. USA. The pollination took place in October 2003 and the seed sowing in April 2004.

The first act of asexual reproduction of 'Mes Azur' was accomplished when vegetative cuttings were taken from the initial selection in the September 2004 in a controlled environment in Gilroy, Calif. USA.

Horticultural examination of plants grown from cuttings of the plant initiated in September 2004 in Gilroy, Calif. USA, and continuing thereafter, has demonstrated that the combination of characteristics as herein disclosed for 'Mes Azur' are firmly fixed and are retained through successive generations of asexual reproduction.

'Mes Azur' has not been observed under all possible environmental conditions. The phenotype may vary significantly with variations in environment such as temperature, light intensity and day length.

A Plant Breeder's Right for this cultivar was applied for in Canada on Dec. 24, 2007. 'Mes Azur' has not been made publicly available more than one year prior to the filing of this application.

DESCRIPTION OF THE DRAWINGS

The accompanying photographic drawing shows typical flower and foliage characteristics of 'Mes Azur' with colors being as true as possible with an illustration of this type. The photographic drawing shows two flowering potted plants of the new variety and a close-up of the flowers, growing in one gallon pots. This plant was grown and photographed in Gilroy, Calif. USA in April 2008. The plant was about 4 months old.

DETAILED BOTANICAL DESCRIPTION

The measurements were taken on plants growing in Gilroy, Calif. USA in April 2008. The plants were growing in gallon pots in a greenhouse trial. These plants were about 4–5 months old.

Color Chart used: Royal Horticultural Society Colour Chart (R.H.S.) 2001.

BRIEF SUMMARY OF INVENTION

The following observations, measurements, and comparisons describe plants grown Gilroy, Calif. USA. The following traits have been repeatedly observed and are determined to be basic characteristics of the new variety. The combination of these characteristics distinguishes this Salvia as a new and distinct variety.

TABLE 1

DIFFERENCES BETWEEN THE NEW CULTIVAR 'MES AZUR' AND A SIMILAR VARIETY

| | 'Mes Azur' | 'Navajo Purple' (Not patented) |
|---|---|---|
| Flower color | Medium violet | Purple |
| Plant habit | More upright | Less upright |
| Foliage size | Larger | Smaller |

Plant:

*Form, growth and habit.*—Upright, well branching, dense and bushy.
*Plant height.*—30–36 cm.
*Plant height (inflorescence included).*—39–42 cm.
*Plant width.*—35–40 cm.

Foliage:

*Type.*—Simple, opposite.
*Immature, leaf color, upper surface.*—Closest to RHS 146B.
*Lower surface.*—RHS 147B.
*Mature, leaf color, upper surface.*—Closest to RHS 146A.
*Lower surface.*—RHS 147B.
*Length.*—5.8–6.1 cm.
*Width.*—2.3–2.6 cm.
*Shape.*—Ovate to elliptical.
*Base shape.*—Attenuate.
*Apex shape.*—Obtuse.
*Margin.*—Crenulate.
*Texture, upper surface.*—Hispid; some glandular hairs.
*Texture, lower surface.*—Hispid.
*Fragrant.*—Heavily "sage" like.
*Color of veins, upper surface.*—RHS 144B.
*Color of veins, lower surface.*—RHS 144B.
*Petioles color.*—RHS 144B.
*Petioles length.*—1.8–2.3 cm.
*Diameter of petiole.*—0.15–0.2 cm.
*Texture.*—Hispid.

Stem:

*Number of main branches per plan.*—3–4.
*Number of leaves per stem.*—10–14.
*Color of stem.*—Between RHS 144A and B.
*Length of stem.*—26–30 cm.
*Diameter.*—0.3–0.4 cm.
*Length of internodes.*—0.25–2.0 cm.
*Texture.*—Hispid; muriculate.

Inflorescence:

*Type.*—Terminal raceme.
*Blooming habit.*—Flowers continuously from spring through the fall.
*Number of racemes per plant.*—50–60.
*Duration of flowering:.*—Continuous flowering throughout the summer.
*Color of peduncle.*—RHS 146A overlaid with RHS N187B.
*Length of peduncle.*—7–16 cm.
*Peduncle diameter.*—0.2 cm.
*Texture.*—Hispid; glandular hairs.
*Color of pedicel.*—RHS 148A.
*Length of pedicel.*—0.4–0.5 cm.
*Diameter of pedicel.*—0.75 cm.
*Texture.*—Hispid; glandular hairs.

Corolla:

*Form.*—Single, bilabiate; one upper lip, with one upper lip, and one lower lip with three lobes consisting one a mid-lobe and 2 small lateral lobes; lips fused at base; upper lip wraps around the pistil.
*Lastingness of individual bloom on the plant.*—3–6 days.
*Fragrance.*—"Sage" like.
*Immature florets.*—
*General color, upper surface.*—RHS N82A.
*Lower surface.*—RHS 85A.
*Mature florets.*—
*Vertical height of floret.*—1.7–1.9 cm.
*Horizontal width of floret.*—2.1–2.2 cm.
*Depth of floret.*—2.6–2.8 cm.
*Color upper lip, upper surface.*—RHS N87B, but appears deeper because of the RHS N87A color of the villous hairs.
*Color upper lip, lower surface.*—RHS N87D.
*Length of upper lip.*—0.8–0.9 cm.
*Width of upper lip.*—0.3 cm.
*Shape.*—Obovate.
*Apex shape.*—Obtuse.
*Margin.*—Entire.
*Texture, outer surface.*—Papillose; villous hairs of RHS N87A at the apex.
*Inner surface.*—Glabrous.
*Color lower lip, mid-lobe, upper surface.*—RHS N87A.
*Color lower lip, mid-lobe, lower surface: RHS N*87D.
*Length of lower lip, mid-lobe.*—1.4–1.5 cm.
*Width of lower lip, mid-lobe.*—1.0–1.3 cm.
*Shape.*—Obovate.
*Apex shape.*—Emarginate.
*Margin.*—Appears very slightly laciniate.
*Texture, upper surface.*—Papillose.
*Lower surface.*—Glabrous.
*Color lower lip, lateral lobe, upper surface.*—RHS N87B.
*Color lower lip, lateral lobe, lower surface.*—RHS N87D.
*Length of lower lip, lateral lobe.*—0.6–0.7 cm.
*Width of lower lip, lateral lobe.*—0.35 cm.
*Shape.*—Oblong.
*Apex shape.*—Rounded.
*Margin.*—Entire.
*Texture, upper surface.*—Papillose.
*Lower surface.*—Glabrous; few hirsute hairs.
*Corolla, color, outer surface.*—RHS N87B.
*Inner surface.*—RHS N87D.
*Length of corolla.*—1.5–1.6 cm.
*Width of corolla.*—0.6–0.7 at widest point.
*Texture, outer upper surface.*—Slightly hispid.
*Texture, outer lower surface.*—Glabrous.
*Texture, inner surfaces.*—Glabrous.

Bud (just before opening):

*Color.*—RHS N88A.
*Length.*—1.1–1.5 cm.
*Width.*—0.2–0.4 cm.
*Shape.*—Tubular to oblong.

Calyx:

*Number of sepals.*—2, fused into a tube form.

*Color of sepals, upper surface, upper most sepal.*—RHS 144B; RHS N187A anthocyanin overlay becoming lighter basally closest to RHS 187B.

*Lower most sepals.*—RHS 144B; slight anthocyanin overlay of a light hue of RHS N186D at the apex.

*Inner surface of all sepals.*—RHS 194A.

*Length of sepals.*—0.8–0.9 cm.

*Width of sepals.*—0.25–0.3 cm.

*Sepal shape.*—Broadly linear.

*Apex shape.*—Acute.

*Margin.*—Entire.

*Texture, outer surface.*—Hispid; muriculate.

*Inner surface.*—Glabrous.

Reproductive organs:

*Pistil.*—1.

*Length.*—2.2—2.3 cm.

*Style color.*—RHS N155B.

*Style length.*—2.1–2.2 cm.

*Stigma color.*—RHS 90C.

*Stamens.*—2.

*Color of filaments.*—RHS N155B.

*Length of filaments.*—1.0 cm.

*Anther color.*—RHS 14A.

*Anther length.*—0.3 cm.

*Color of pollen.*—RHS 17B.

*Pollen amount.*—Moderate.

*Fertility/seed set.*—Not observed on this hybrid.

Disease/pest resistance: Disease resistance or susceptibility has not been observed on this hybrid.

What is claimed is:

1. A new and distinct variety of *Salvia* plant named 'Mes Azur,' substantially as illustrated and described herein.

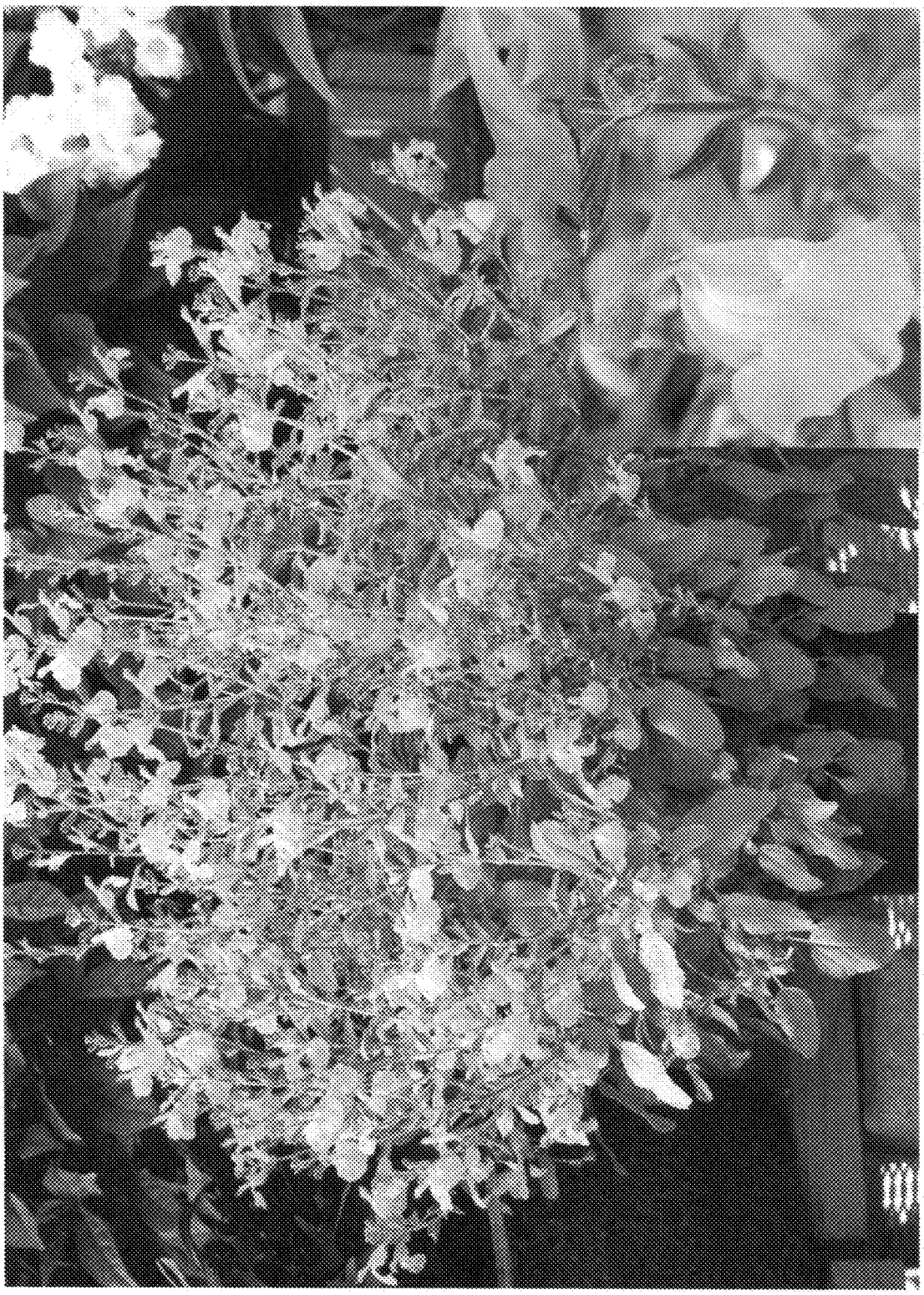

* * * * *